(12) United States Patent
Chang et al.

(10) Patent No.: US 12,239,355 B2
(45) Date of Patent: Mar. 4, 2025

(54) BALLOON CATHETER AND ABLATION SYSTEM

(71) Applicant: SHANGHAI MICROPORT EP MEDTECH CO., LTD., Shanghai (CN)

(72) Inventors: Zhaohua Chang, Shanghai (CN); Bo Liang, Shanghai (CN); Yiyong Sun, Shanghai (CN); Liuping Shen, Shanghai (CN)

(73) Assignee: SHANGHAI MICROPORT EP MEDTECH CO., LTD., Shanghai (CN)

(*) Notice: Subject to any disclaimer, the term of this patent is extended or adjusted under 35 U.S.C. 154(b) by 911 days.

(21) Appl. No.: 17/419,219

(22) PCT Filed: Nov. 15, 2019

(86) PCT No.: PCT/CN2019/118882
§ 371 (c)(1),
(2) Date: Jun. 28, 2021

(87) PCT Pub. No.: WO2020/134683
PCT Pub. Date: Jul. 2, 2020

(65) Prior Publication Data
US 2022/0110669 A1    Apr. 14, 2022

(30) Foreign Application Priority Data

Dec. 28, 2018 (CN) .......................... 201811653052.3

(51) Int. Cl.
*A61B 18/04* (2006.01)
*A61B 18/00* (2006.01)
*A61B 18/02* (2006.01)

(52) U.S. Cl.
CPC .............. *A61B 18/04* (2013.01); *A61B 18/02* (2013.01); *A61B 2018/0022* (2013.01);
(Continued)

(58) Field of Classification Search
None
See application file for complete search history.

(56) References Cited

U.S. PATENT DOCUMENTS 4,946,460 A * 8/1990 Merry .................... A61B 18/02
606/24
6,283,959 B1 * 9/2001 Lalonde ................. A61B 18/02
606/23
(Continued)

FOREIGN PATENT DOCUMENTS

CN    2671511 Y    1/2005
CN    1674836 A    9/2005
(Continued)

*Primary Examiner* — Ronald Hupczey, Jr.
(74) *Attorney, Agent, or Firm* — Muncy, Geissler, Olds & Lowe, P.C.

(57) ABSTRACT

An electrophysiological catheter and an ablation system comprising a control device, an ablation energy output device and the electrophysiological catheter. The control device controls the ablation energy output device to selectively provide a first fluid or a second fluid that is a frozen liquid to the electrophysiological catheter. When the ablation energy output device provides the first fluid, the control device controls a first heating component on the electrophysiological catheter to work to heat the fluid entering the electrophysiological catheter for spraying a thermal ablation gas onto the inner surface of a balloon; and when the ablation energy output device provides frozen liquid, the control device controls the first heating component not to work to directly spray the frozen liquid to the inner surface of the balloon.

18 Claims, 5 Drawing Sheets

(52) U.S. Cl.
CPC ............ *A61B 2018/00351* (2013.01); *A61B 2018/00577* (2013.01); *A61B 2018/00714* (2013.01); *A61B 2018/00797* (2013.01); *A61B 2018/00916* (2013.01); *A61B 2018/0212* (2013.01); *A61B 2018/048* (2013.01)

(56) References Cited

U.S. PATENT DOCUMENTS

| | | | |
|---|---|---|---|
| 7,938,822 B1* | 5/2011 | Berzak | A61B 18/02 606/22 |
| 9,636,172 B2 | 5/2017 | Hu | |
| 2004/0243119 A1 | 12/2004 | Lane et al. | |
| 2006/0122590 A1* | 6/2006 | Bliweis | A61B 18/02 606/24 |
| 2009/0118723 A1* | 5/2009 | Lalonde | A61B 18/02 606/22 |
| 2014/0163539 A1 | 6/2014 | DeLonzor et al. | |
| 2015/0005676 A1 | 1/2015 | Zerins et al. | |
| 2015/0018809 A1 | 1/2015 | Mihalik | |
| 2016/0242835 A1 | 8/2016 | Ramadhyani et al. | |
| 2017/0312027 A1 | 11/2017 | Harlev et al. | |
| 2018/0333192 A1 | 11/2018 | Sliwa et al. | |

FOREIGN PATENT DOCUMENTS

| | | |
|---|---|---|
| CN | 1901844 A | 1/2007 |
| CN | 102438538 A | 5/2012 |
| CN | 202637100 U | 1/2013 |
| CN | 103079487 A | 5/2013 |
| CN | 103209655 A | 7/2013 |
| CN | 103442631 A | 12/2013 |
| CN | 103547229 A | 1/2014 |
| CN | 103917184 A | 7/2014 |
| CN | 105228542 A | 1/2016 |
| CN | 105682589 A | 6/2016 |
| CN | 106061421 A | 10/2016 |
| CN | 106102816 A | 11/2016 |
| CN | 106880400 A | 6/2017 |
| CN | 108135496 A | 6/2018 |
| CN | 108135645 A | 6/2018 |
| CN | 108366820 A | 8/2018 |
| CN | 207693670 U | 8/2018 |
| EP | 1773224 B1 | 1/2017 |
| WO | WO-00/56237 | 9/2000 |
| WO | WO-2011/142909 A1 | 11/2011 |
| WO | WO-2015/006854 A1 | 1/2015 |
| WO | WO-2018/089773 A1 | 5/2018 |
| WO | WO-2018/226751 A1 | 12/2018 |

* cited by examiner

BALLOON CATHETER AND ABLATION SYSTEM

TECHNICAL FIELD

The present application relates to the field of medical instruments and, in particular, to a balloon catheter and an ablation system.

BACKGROUND

Patients with atrial fibrillation are at very high risk for stroke. In atrial fibrillation, the atrium has a rapid and irregular beating and losses the contractility. This makes it easy for blood to stagnate in the atrium and form a thrombus. When such thrombus falls off and travels through the arteries to the brain, a stroke may occur. This can be treated by applying energy to the pulmonary vein for ablation via the interventional catheter to isolate the pulmonary vein potential. Hypertension is characterized by high prevalence, low awareness and significant harmfulness. Experimental data has suggested a correlation of hypertension to elevated renal sympathetic nerve excitability. Blocking the renal sympathetic nerves through ablation can not only lower blood pressure, but also benefit organ-specific chronic diseases arising from the hyperactivation of sympathetic nerve.

Ablation can be accomplished with a cryoballoon ablation, which is designed based on anatomical considerations and makes use of the contact between balloon and a target tissue for freezing. Cryoballoon ablation is characterized by the ability to form a continuous ablation within a single procedure. Specifically, the cryoballoon catheter having its distal end provided with a balloon and its proximal end connected to refrigerating installation is used. During the operation, a physician may place the catheter through a percutaneous puncture into the heart and reaches the pulmonary vein ostium. The balloon is then dilated and contact between an outer wall of balloon and myocardial tissue is adjusted. Then, a frozen liquid is sprayed from a liquid inlet pipe of the catheter directly onto an inner surface of the balloon. The frozen liquid instantly vaporizes and absorbs heat conducted from myocardial temperature to cool the tissue that is in contact with the balloon, thereby achieving cryoablation. Apart from cryoablation, thermal ablation accomplished by ablation electrode can also be used. The ablation method of the ablation electrode is similar to that of the cryoballoon ablation. Specifically, the ablation electrode-based balloon catheter having its distal end provided with a balloon and its proximal end connected to ablation apparatus is used. During the operation, a physician may place the ablation electrode-based balloon catheter through a percutaneous puncture into the heart and reaches the pulmonary vein ostium. The balloon is then dilated and contact between an outer wall of balloon and myocardial tissue is adjusted. Then, heat may be delivered from the ablation electrode to ablate the target tissue to achieve thermal ablation.

The inventors have found that, it has been proposed to arrange a heating wire within a cryoablation catheter, which can shorten rewarming of the freezing process by heating the heating wire and thus reduce the overall procedure time. Additionally, some have proposed solutions to solve the problem that an uneven balloon surface temperature of an ablation balloon catheter would burn the tissue, in order to achieve better treatments of ablation. However, all existing techniques employ a single ablation pattern, i.e., either cryogenic or thermal ablation, making therapeutic effect of ablation still not ideal.

SUMMARY

An object of present application is to provide a balloon catheter and an ablation system, which are intended to achieve the combined cryogenic and thermal ablation with a single set of ablation system so as to provide an improved ablation treatment.

To achieve the above object, present application provides a balloon catheter comprising a catheter body and a balloon that is disposed at a distal end of the catheter body. The balloon catheter further comprises a first heating component and a first temperature sensor and the catheter body comprises a fluid transportation pipe. The fluid transportation pipe has a distal end disposed within the balloon to release a fluid into the balloon, the first heating component arranged at the distal end of the fluid transportation pipe to heat the fluid in the fluid transportation pipe, the first temperature sensor arranged at the distal end of the catheter body or on the first heating component to capture temperature information of the catheter body or the first heating component.

When the first heating component is operating, the fluid transportation pipe is configured to release a thermal ablation gas into the balloon; and when the first heating component is not operating, the fluid transportation pipe is configured to release a frozen liquid into the balloon.

Optionally, the balloon catheter further comprises a second heating component and a second temperature sensor. The second heating component is disposed at a proximal end of the fluid transportation pipe to pre-heat the fluid entering the fluid transportation pipe, the second temperature sensor disposed at a proximal end of the catheter body or on the second heating component to capture temperature information of the catheter body or the second heating component.

When the first and second heating components are operating concurrently, the fluid transportation pipe is configured to release a thermal ablation gas into the balloon; and when none of the first and second heating component is operating, the fluid transportation pipe is configured to release a frozen liquid into the balloon.

Optionally, the fluid transportation pipe comprises a first helical section and a first longitudinally extending section in communication with the first helical section. The first heating component is disposed on the first longitudinally extending section, and the first temperature sensor is arranged on the fluid transportation pipe at a location close to a distal end of the first heating component.

Optionally, the first helical section is provided with a plurality of fluid spraying orifices. The plurality of fluid spraying orifices are configured to spray the fluid towards different directions.

Optionally, the balloon catheter further comprises a handle coupled to the proximal end of the catheter body. The second heating component is disposed within the handle.

Optionally, the handle comprises at least one electrical input/output interface, one fluid inlet interface and one fluid outlet interface.

the fluid inlet interface is in communication with the proximal end of the fluid transportation pipe, the at least one electrical input/output interface coupled to the first heating component, the first temperature sensor, the second heating component and the second temperature sensor, the fluid outlet interface configured to exhaust the fluid in the catheter body out of the catheter body.

Optionally, the second temperature sensor is disposed on the fluid transportation pipe at a location close to a distal end of the second heating component.

Optionally, the first heating component comprises a second helical section and a second longitudinally extending section electrically connected to the second helical section. The second helical section is wound around the fluid transportation pipe, and the second longitudinally extending section extends along a pipe wall of the fluid transportation pipe and comes into connection with an electrical input/output interface at the proximal end of the catheter body.

Optionally, the first heating component and/or second heating component are/is an electrical resistance wire or induction coil.

Optionally, the balloon catheter further comprises a third heating component and a third temperature sensor, the third heating component disposed on the balloon to heat a target zone, the third temperature sensor disposed on the balloon to capture temperature information of the third heating component.

Optionally, the balloon catheter further comprises fourth temperature sensor(s) disposed on the balloon and/or on the catheter body to capture temperature information of the balloon and/or catheter body.

Optionally, the catheter body further comprises an outer tube and a hollow core shaft, each of the fluid transportation pipe and the core shaft sleeved within the outer tube, the core shaft movably arranged within the outer tube. The balloon has its distal end to be connected to the core shaft and proximal end to be connected to the outer tube. The distal end of the fluid transportation pipe is helically wound around the core shaft.

To achieve the above object, present application provides an ablation system comprising a control device, an ablation energy output device and the balloon catheter as defined above. The ablation energy output device is in communication with the balloon catheter and is configured to supply a fluid to the balloon catheter.

The control device is configured to control the ablation energy output device to selectively supply a first or second fluid to the fluid transportation pipe, the second fluid being a frozen liquid.

The control device is further configured to, when the ablation energy output device supplies the first fluid to the fluid transportation pipe, control the first heating component to operate such that the first heating component heats the first fluid entering the fluid transportation pipe to make the fluid transportation pipe spray a thermal ablation gas to the balloon; and simultaneously control a heating temperature of the first heating component based on temperature information fed back by the first temperature sensor such that a surface temperature of the balloon is in a predetermined thermal ablation temperature range.

The control device is further configured to, when the ablation energy output device supplies the second fluid to the fluid transportation pipe, control the first heating component not to operate such that the fluid transportation pipe sprays the frozen liquid to the balloon.

Optionally, in case that the balloon catheter further comprises the second heating component and the second temperature sensor, the control device is further configured to, when the ablation energy output device supplies the first fluid to the fluid transportation pipe, further control the second heating component to operate such that the second heating component pre-heats the fluid just entering the fluid transportation pipe; and simultaneously control a heat temperature of the second heating component based on temperature information fed back by the second temperature sensor.

Optionally, the ablation energy output device comprises a fluid source, a heating unit, a refrigerating unit and a fluid output channel.

The fluid source is configured to store fluid, and the fluid output channel is in communication with the fluid source to transport the fluid in the fluid source. The refrigerating unit is disposed on the fluid output channel to refrigerate the fluid in the fluid output channel, and the heating unit is configured to provide the first heating component and/or second heating component with a heating energy.

The control device is further configured to, when the ablation energy output device supplies the second fluid to the fluid transportation pipe, control the refrigerating unit to refrigerate the fluid flowing in the fluid output channel such that the ablation energy output device supplies the fluid transportation pipe with the frozen liquid.

The control device is further configured to, when the ablation energy output device supplies the first fluid to the fluid transportation pipe, control the heating unit to provide the first heating component with a heating energy such that the first heating component heats the fluid flowing in the fluid output channel or to provide the first and second heating components with a heating energy such that the first and second heating components heat the fluid flowing in the fluid output channel.

Optionally, the predetermined thermal ablation temperature range is from 50° C. to 80° C.

Optionally, the fluid is carbon dioxide or nitrous oxide.

Optionally, the refrigerating unit is a compressor, and the heating unit is a high-frequency heat source or a normal power source capable of heating an electrical resistance wire.

Optionally, the control device comprises a refrigerating control unit and heating control unit.

The refrigerating unit is configured to refrigerate the fluid flowing in the fluid output channel based on a refrigerating signal sent from the refrigerating control unit; and the heating unit is configured to supply the first heating component and/or the second heating component with heating energy based on a heating signal sent from the heating control unit.

Optionally, the balloon catheter further comprises a third heating component and a third temperature sensor, which are both disposed on the balloon.

The control device is further configured to, when the ablation energy output device stops supplying the fluid to the fluid transportation pipe or starts to supply the first fluid to the fluid transportation pipe, control the heating unit to provide the heating energy to the third heating component such that the third heating component heats a target tissue, and simultaneously control a heating temperature of the third heating component based on temperature information of the third heating component fed back by the third temperature sensor.

Optionally, the balloon catheter further comprises fourth temperature sensor(s) disposed on the balloon and/or on the catheter body.

The control device is further configured to modulate a cryoablation temperature or a thermal ablation temperature based on temperature information of the balloon and/or catheter body fed back by the fourth temperature sensor(s).

Optionally, the ablation system further comprises a display device for displaying the temperature information fed back by any of the first, second, third and fourth temperature sensors.

Optionally, the control device is configured to, control the ablation energy output device to supply the second fluid to the balloon catheter for a duration of time and then to supply the first fluid to the balloon catheter, and simultaneously control the ablation energy output device to supply the first heating component with a heating energy or to supply the first heating component and the second heating component with a heating energy, so as to perform at least one thermal ablation cycle following at least one cryoablation.

In the above balloon catheter and ablation system, through the first heating component arranged on the distal end of the fluid transportation pipe, the purpose of heating a fluid in the fluid transportation pipe is able to be achieved so that the distal end of the fluid transportation pipe is able to spray a thermal ablation gas onto the inner surface of the balloon, enabling thermal ablation of a target tissue. Additionally, when the first heating component in the balloon catheter is out of operation, a frozen liquid is able to be sprayed onto the inner surface of the balloon to allow cryoablation of the target tissue. In this way, combined cryogenic and thermal ablation to the target tissue is able to be achieved, resulting in an improved therapeutic effect of ablation. Further, switching between the cryoablation and thermal ablation modes does not require removals or reinsertions of the balloon catheter, avoiding secondary damages to the patient that may arise from removals or reinsertions of the balloon catheter and further improving operation treatment effect.

Moreover, switching between the cryoablation and thermal ablation modes does not require relocating the balloon. That is, the balloon is able to accomplish both cryoablation and thermal ablation to the same tissue at the same position. This allows avoiding the problem of incomplete ablation existed in cryoablation alone or thermal ablation alone, thereby leading to an improved therapeutic effect of ablation, as well as a shortened operation time and increased operation efficiency. Moreover, in present application, free switching between the cryoablation and thermal ablation modes is achievable under the control of the control device, which allows a convenient operation and an improved operation efficiency.

Further preferably, the balloon catheter also includes the second heating component and the second temperature sensor. The second heating component enables to pre-heat a fluid as soon as it enters the balloon catheter. This allows protecting the human body from a sudden temperature change around the catheter's distal end, thereby ensuring the safety of the system and improving heating efficiency.

BRIEF DESCRIPTION OF THE DRAWINGS

In order to more clearly explain embodiments of present application or technical solutions of the prior art, the accompanying drawings needed to be used in the description of the embodiments or the prior art will be briefly introduced below. Apparently, these drawings in the following description merely show some embodiments of present application, and those of ordinary skill in the art can obtain other drawings in light of those contained drawings, without paying any creative effort.

Figure 1:
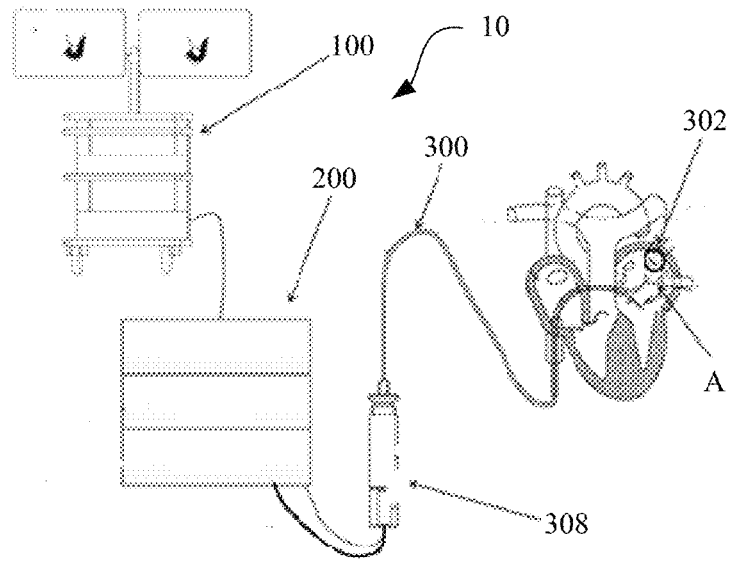
FIG. 1 schematically illustrates the cardiac ablation performed by an ablation system according to an embodiment of present application.

In the figures,
10, ablation system;
100, control device; 110, refrigerating control unit; 120, heating control unit;
200, ablation energy output device; 210, refrigerating unit; 220, heating unit; 230, fluid output channel; 240, fluid source; 250, fluid input channel;
300, electrophysiology catheter; 301, catheter body; 302, balloon; 303, first heating component; 303a, second helical section; 303b, second longitudinally extending section; 304, first temperature sensor; 305, fluid transportation pipe; 305a, first helical section; 305b, first longitudinally extending section; 305c, fluid spraying orifice; 306, second heating component; 306a, third helical section; 306b, third longitudinally extending section; 307, second temperature sensor; 308, handle; 3081, lumen interface; 3082, heating energy input/output interface; 3083, temperature sensor communication interface; 3084, fluid inlet interface; 3085, fluid outlet interface; 309, outer tube; 310, core shaft; 311, radiopaque marker; 312, third heating component; 313, third temperature sensor; 314, fourth temperature sensor;
A, pulmonary vein; B, renal artery ostium; C, renal artery; Q, target zone; L, lead.

DETAILED DESCRIPTION

The present application will be described in greater detail with reference to the accompanying drawings so that the invention will become more apparent and readily understood. Of course, the present application is not limited to the following specific examples, and general replacements well known to those skilled in the art are also embraced within the scope thereof. Additionally, while the present application is described in detail with reference to schematic figures, these figures are presented only for the purpose of facilitating the detailed description of the examples rather than limiting present application in any sense.

As used herein, the terms "proximal" and "distal" describe relative orientations, relative positions and directions between elements or actions, viewed by a physician operating the product. Without wishing to be limiting, a "proximal end" usually refers to an end of the product close to the physician during normal operation, while a "distal end" usually refers to an end thereof that enters the patient's body first. As used in the specification, and in the appended claims, the singular forms "a", "an" and "the" include plural referents unless the context clearly dictates otherwise. As used in the specification, and in the appended claims, the term "or" is employed in the sense including "and/or" unless the context clearly dictates otherwise.

As described above in the background section, there is no technical solution of combined cryogenic and thermal ablation provided in prior art.

Through extensive research, in one embodiment, present application provides an electrophysiology catheter including a catheter body and a balloon provided at a distal end of the catheter body. The electrophysiology catheter further includes a first heating component and a first temperature sensor, and the catheter body includes a fluid transportation pipe. A distal end of the fluid transportation pipe is disposed in the balloon and configured to release a fluid into the balloon. The first heating component is disposed at the distal end of the fluid transportation pipe and configured to heat the fluid in the fluid transportation pipe. The first temperature sensor is arranged at the distal end of the catheter body or on the first heating component and is configured to capture temperature information of the catheter body or the first heating component. When the first heating component is operating, the fluid transportation pipe is configured to release a thermal ablation gas into the balloon; and when the first heating component is not operating, the fluid transportation pipe is configured to release a frozen liquid into the balloon.

Further provided is an ablation system including a control device, an ablation energy output device and the electrophysiology catheter. The ablation energy output device is in communication with the electrophysiology catheter and is configured to supply the electrophysiology catheter with a fluid.

The control device is configured to control the ablation energy output device to selectively supply a first or second fluid to the fluid transportation pipe. The second fluid is a frozen liquid.

The control device is also configured to, when the ablation energy output device supplies the first fluid to the fluid transportation pipe, control the first heating component to operate such that the first heating component heats the first fluid entering the fluid transportation pipe to make the fluid transportation pipe spray a thermal ablation gas to the balloon; and simultaneously control a heating temperature of the first heating component based on temperature information fed back by the first temperature sensor such that a surface temperature of the balloon is in a predetermined thermal ablation temperature range.

Moreover, the control device is also configured to, when the ablation energy output device supplies the second fluid to the fluid transportation pipe, control the first heating component not to operate such that the fluid transportation pipe sprays the frozen liquid to the balloon.

The above objects, features and advantages of the present application will become more apparent and readily understood from the following detailed description of particular embodiments in conjunction with the accompanying drawings.

Figure 2:
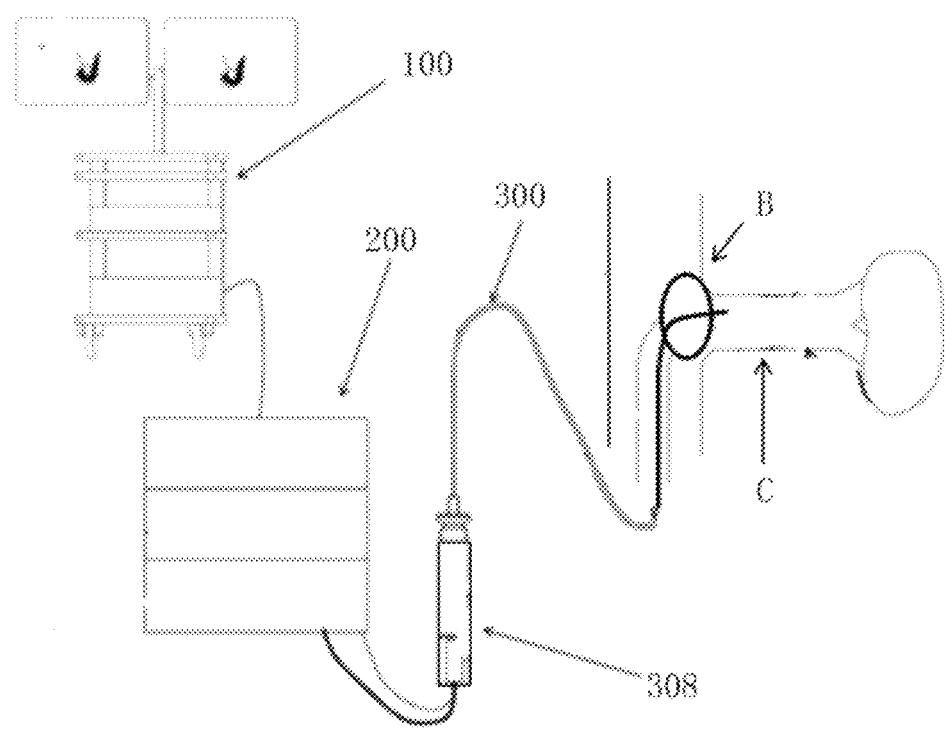
FIG. 2 schematically illustrates the renal artery ablation performed by the ablation system according to an embodiment of present application.

Reference is now made to FIG. 1 which schematically illustrates the cardiac ablation performed by the ablation system according to an embodiment of present application, and to FIG. 2, which schematically illustrates the renal artery ablation performed by the ablation system according to an embodiment of present application.

As shown in FIGS. 1 and 2, the ablation system 10 according to embodiments of present application includes a control device 100, an ablation energy output device 200 and an electrophysiology catheter 300. The ablation energy output device 200 is in fluid communication with the electrophysiology catheter 300 so as to be able to supply an ablation fluid to the electrophysiology catheter 300. In some embodiments, the control device 100 is coupled to the ablation energy output device 200, which is in turn connected to the electrophysiology catheter 300. In some other embodiments, the control device 100 is coupled to both the ablation energy output device 200 and the electrophysiology catheter 300. In yet some other embodiments, the control device 100 and the ablation energy output device 200 is integrated in a single device. The present application is not limited in this regard.

The ablation system 10 is configured to perform the combined cryogenic and thermal ablation on a target tissue so as to improve treatment effect of ablation. The target tissue may be, but is not limited to, the heart, a renal artery or the like. For example, as shown in FIG. 1, the ablation system 10 is used in a cardiac therapy, in which the electrophysiology catheter 300 is inserted into the heart using an interventional technique in order to perform ablation on the pulmonary vein A (that is, using the balloon to occlude the pulmonary vein for ablation) for treating a cardiac arrhythmia. Or, as shown in FIG. 2, the ablation system 10 may also be applied to the renal artery, in which the electrophysiology catheter 300 is placed at the renal artery ostium B of the renal artery C using an interventional technique to perform ablation of the renal artery for adjusting blood pressure of the renal artery.

The structure of the electrophysiology catheter 300 will be described in greater detail below with reference to FIGS. 3a to 3d.

Figure 3A:
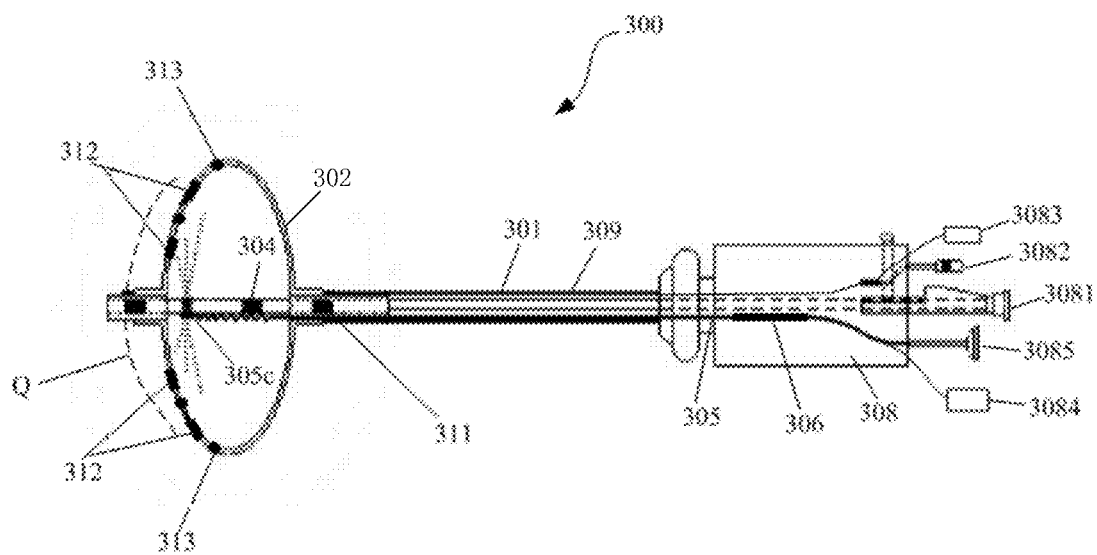
FIG. 3a schematically illustrates the overall structure of an electrophysiology catheter according to an embodiment of the present application.
Figure 3B:
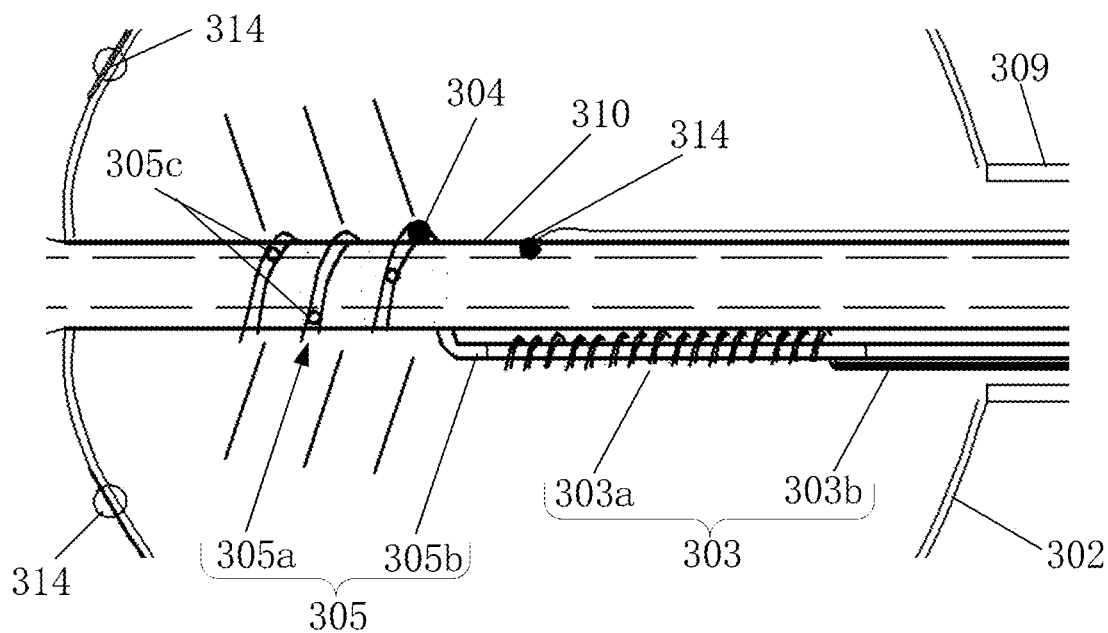
FIG. 3b is a structural schematic of a distal end of the electrophysiology catheter according to an embodiment of the present application.

As shown in FIGS. 3a and 3b, the electrophysiology catheter 300 includes a catheter body 301, a balloon 302, a first heating component 303 and a first temperature sensor 304. The balloon 302 is arranged on the catheter body 301 and located at a distal end of the catheter body 301. The catheter body 301 includes a fluid transportation pipe 305. The distal end of the fluid transportation pipe 305 is arranged in the balloon 302 and configured to spray a frozen liquid or thermal ablation gas onto an inner surface of the balloon 302. The balloon 302 may be made of a material having a good temperature resistance, such as polyester, nylon or fluoroplastic.

The first heating component 303 is disposed on the fluid transportation pipe 305, particularly at the distal end of the fluid transportation pipe 305. The first heating component 303 is also arranged within the balloon 302 in order to ensure the safety of the system. The first heating component 303 is configured to heat a fluid in the fluid transportation pipe 305 so that the fluid transportation pipe 305 sprays a thermal ablation gas onto the inner surface of the balloon 302. The first temperature sensor 304 is arranged at the distal end of the catheter body 301 to capture temperature information of the catheter body 301. Alternatively, the first temperature sensor 304 is arranged on the first heating component 303 to capture temperature information of the first heating component 303. Still alternatively, two or more first temperature sensors 304 are provided respectively at the distal end of the catheter body 301 and on the first heating component 303 so as to capture temperature information of the catheter body 301 and the first heating component 303 respectively. In preferred embodiments of the present application, the first temperature sensor 304 is provided on the fluid transportation pipe 305 and at a location near the distal end of the first heating component 303.

In practical use, the control device 100 controls the ablation energy output device 200 to selectively supply a first or second fluid to the electrophysiology catheter 300. Here, the second fluid is a frozen liquid, namely, a refrigerated liquid, and the first fluid may be a frozen liquid, or a liquid or gas or a gas/liquid mixture at the ambient temperature that have not been refrigerated.

More specifically, when the ablation system 10 is used for cryoablation to a target tissue, the control device 100 controls the ablation energy output device 200 to directly supply the electrophysiology catheter 300 with a frozen liquid. At the same time, the control device 100 also controls the first heating component 303 not to heat, so that the fluid transportation pipe 305 sprays a frozen liquid (i.e., the second fluid) supplied by the ablation energy output device 200 onto the inner surface of the balloon 302 directly. When the ablation system 10 is used for thermal ablation of a target tissue, the control device 100 controls the ablation energy output device 200 to supply the electrophysiology catheter 300 with the first fluid and simultaneously control the first heating component 303 to heat the first fluid in the fluid transportation pipe 305, so that the fluid transportation pipe 305 sprays a thermal ablation gas onto the inner surface of the balloon 302 directly. Moreover, during the thermal ablation, the control device 100 also controls heat heating temperature of the first heating component 303 based on temperature information fed back by the first temperature sensor 304, thus keeping a surface temperature of the balloon within a predetermined thermal ablation temperature to ensure the thermal ablation effect. Here, in the cryoablation and thermal ablation, for example, of the pulmonary vein A by the ablation system 10, it is unnecessary to adjust position of the balloon, allowing cryoablation and thermal ablation of a same target tissue to be performed at the same operating position. Such a way of ablation is able to effectively prevent recurrence of cardiac arrhythmia and improve ablation effect as well as save operation time and enhance operation efficiency.

The working principles of the ablation system 10 will be further explained below in the exemplary context of renal artery ablation with reference to FIG. 4.

Figure 4:
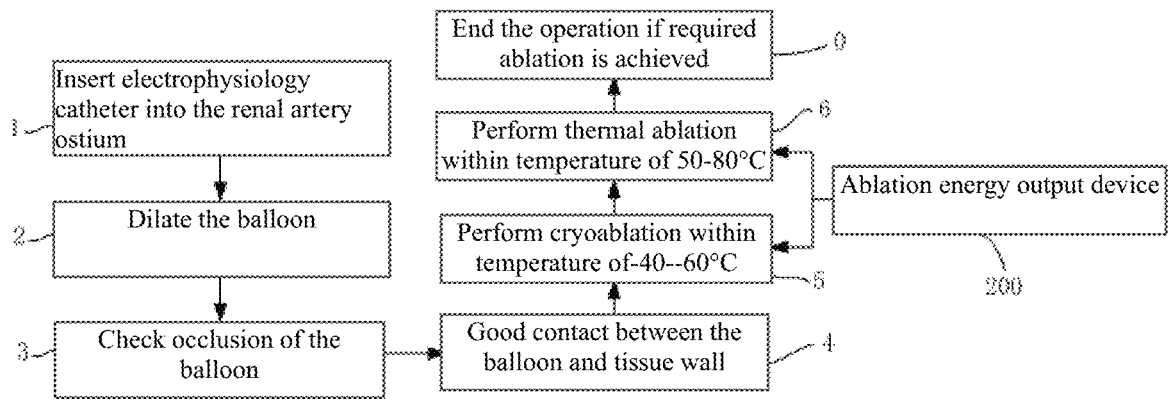
FIG. 4 is a schematic diagram showing the working principle of the ablation system according to an embodiment of the present application.

As shown in FIGS. 2 and 4, first of all, in step 1, the electrophysiology catheter 300 is inserted into the the renal artery ostium B. Afterward, in step 2, the balloon 302 is dilated by filling gas therein. In step 3, occlusion achieved by the balloon is checked (particularly, occlusion of the balloon is checked by occlusion of the blood flow in the renal artery. The complete occlusion of the blood flow indicates the good contact between an outer surface of the balloon and a wall of the tissue), and positional adjustments are made to the balloon if the occlusion of balloon is found to be unsatisfactory, until the state of a good contact between the balloon and the tissue wall is achieved in step 4. Then, the ablation energy output device 200 is controlled to supply the electrophysiology catheter 300 with the first or second fluid.

Following step 4, taking a cryoablation operation carried out first as an example, the ablation energy output device 200 supplies a frozen liquid (i.e., the second fluid) to the electrophysiology catheter 300, causing a surface temperature of the balloon to drop to a desired value (e.g., from −40° C. to −60° C.), so as to enable achievement of cryoablation to the target tissue. This cryoablation operation may be performed only once or repeated several times, and the duration of each operation and number of times of the operation may be determined by physician primarily based on the patient's electrocardiogram. The present application does not put any limitation in this regard. In practical use, in order to ablate the abnormal electrocardiographic tissue thoroughly, the ablation system 10 is switched to a thermal ablation mode after one or more times of cryoablation, in which the control device 100 controls the first heating component 303 to heat the first fluid in the fluid transportation pipe 305, raising the balloon's surface temperature to a required temperature (e.g., from 50° C. to 80° C.) of a thermal ablation, so as to achieve thermal ablation to the target tissue. Likewise, the number of thermal ablation cycles and the duration of each cycle may depend on the actual requirements of the operation, and the present application does not put any limitation in this regard. In this way, the ablation system 10 has the functions of both cryogenic and thermal ablation, facilitating to perform at least one thermal ablation cycle following one or more cryoablation cycles. This enables to ablate abnormal electrocardiographic tissues more thoroughly and thus result in a promoted ablation effect. Moreover, there is no need to insert or remove the electrophysiology catheter 300 in switching between the cryoablation and thermal ablation modes, avoiding secondary damages arising from the insertion or removal of the catheter to the patient, and promoting therapeutic effect of the operation. Furthermore, free switching between the cryoablation and thermal ablation modes under the control of the control device 100 allows achieving a convenient operation and increased operation efficiency.

Further, the fluid transportation pipe 305 includes the first helical section 305a at the distal end thereof and a first longitudinally extending section 305b in fluid communication with the first helical section 305a. The first helical section 305a is provided with a plurality of fluid spraying orifices 305c, which is configured to spray the fluid towards various directions to allow uniform refrigerating or heating of the balloon surface. The first helical section 305a includes two or more wraps. In one embodiment, the plurality of fluid spraying orifices 305c are circumferentially spaced from one another on the most distal wrap of the first helical section 305a. Alternatively, the plurality of fluid spraying orifices 305c are circumferentially spaced from one another on different wraps (which may be adjacent wraps or not adjacent wraps) of the first helical section 305a. Yet alternatively, the plurality of fluid spraying orifices 305c are circumferentially spaced from one another on a single wrap, as well as circumferentially spaced from one another on different wraps. All such embodiments allow the spraying of a fluid towards different angles. More preferably, the fluid spraying orifices 305c spray the fluid in a helical pattern along an axial direction of the first helical section 305a, which allows an even more uniform refrigerating or heating of the balloon surface, thus additionally improving the effect of ablation treatments. The fluid exhausted from the fluid spraying orifices 305c in the form of a gas, a liquid or a gas/liquid mixture expands and/or fills up an internal volume of the balloon 302 to cause the surface of balloon to have a desired ablation temperature, which is exhausted out of the catheter body 301 after heat exchange. The catheter body 301 further includes a fluid exhaust pipe (not shown) which communicates with the internal volume of the balloon 302 in order to recover the fluid after heat exchange. The first longitudinally extending section 305b extends along an axial direction of the catheter body 301 and is configured to be in communication with the ablation energy output device 200.

In embodiments of present application, the first heating component 303 is arranged at a distal end of the first longitudinally extending section 305b, preferably close to the first helical section 305a. In this way, the fluid is heated by the first heating component 303 before it enters the first helical section 305a and is immediately sprayed onto the inner surface of the balloon after heated. This enables to minimize heat loss and ensure good heating efficiency. A plurality of first heating component 303 may be provided. The plurality of first heating component 303 may be arranged side by side along the axial direction of the fluid transportation pipe 305.

Further, the first heating component 303 includes a second helical section 303a and a second longitudinally extending section 303b connected to the second helical section 303a. The second helical section 303a is wound around the first longitudinally extending section 305b and entirely arranged within the balloon 320. This allows ensuring the safety of the system. Optionally, the second helical section 303a may be implemented as an electrical resistance wire or an induction coil, which, when energized, are able to heat a fluid in the fluid transportation pipe 305. The second longitudinally extending section 303b may be a wire jacketed by an insulating layer. The second longitudinally extending section 303b extends along the wall of the first longitudinally extending section 305b up to a proximal end of the catheter body 301, where it is coupled to an electrical input/output interface and hence to the control device 100 or the ablation energy output device 200 so as to receive inputted external power.

Further, in some embodiments, the first temperature sensor 304 is arranged on the first helical section 305a of the fluid transportation pipe 305, preferably close to a distal end of the second helical section 303a. A plurality of first temperature sensors 304 may be provided at different locations of the first helical section 305a. In some other embodiments, the first temperature sensor 304 is disposed on the first longitudinally extending section 305b of the fluid transportation pipe 305, preferably close to the distal end of the second helical section 303a. In still other embodiments, at least one first temperature sensor 304 is arranged on the first helical section 305a, and at least one first temperature sensor 304 is disposed on the first longitudinally extending section 305b. However, the number and positions of the first temperature sensors 304 may vary depending on the actual requirements, which are not limited in present application.

With continued reference to FIG. 3a, preferably, the electrophysiology catheter 300 further includes a second heating component 306 disposed on the fluid transportation pipe 305, specifically at a proximal end of the fluid transportation pipe 305, i.e., a proximal end of the first longitudinally extending section 305b. More preferably, the second heating component 306 is disposed in the handle 308 to ensure the safety of the system. The second heating component 306 is used to heat a fluid that has just flowed into the fluid transportation pipe 305 to a safe temperature (e.g., about 37° C.) that the human body can tolerate. After that, the fluid is heated to a higher temperature suitable for the ablation purpose by the first heating component 303. This can protect the human body from being harmed by a sudden quick temperature rise of the fluid at the catheter's distal end, thus ensuring the safety of the system. It can also result in an improvement in heating efficiency. A plurality of second heating component 306 may be provided. Preferably, the plurality of second heating components 306 are arranged side by side along the axial direction of the fluid transportation pipe 305.

Figure 3C:
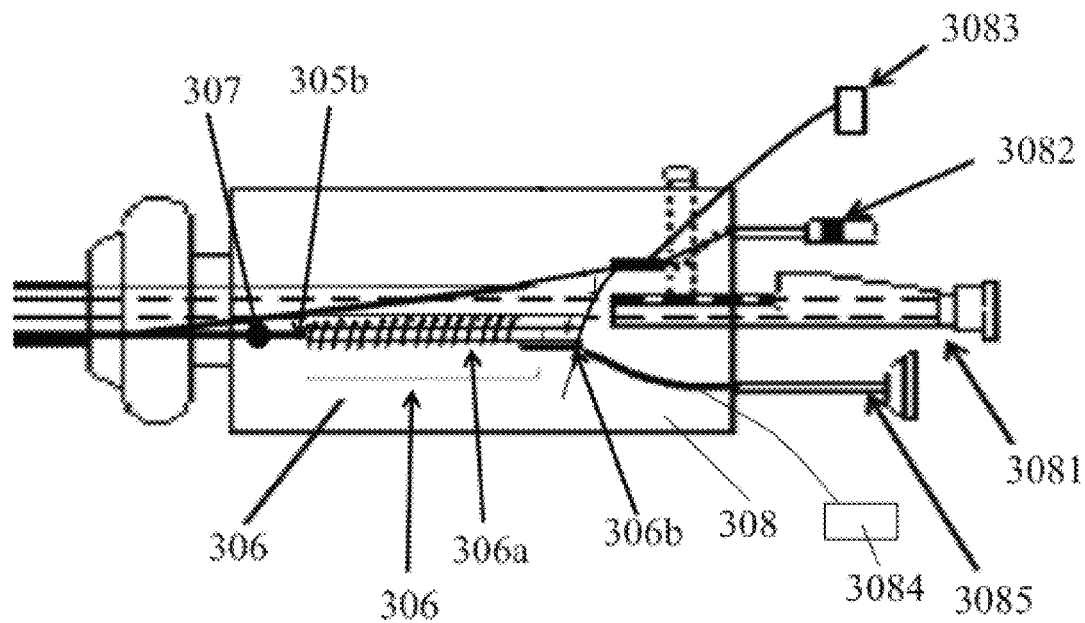
FIG. 3c is a structural schematic of a proximal end of the electrophysiology catheter according to an embodiment of the present application.

Further, as shown in FIG. 3c, the second heating component 306 includes a third helical section 306a and a third longitudinally extending section 306b coupled to the third helical section 306a. The third helical section 306a is wound around the first longitudinally extending section 305b and entirely disposed in the handle 308 in order to ensure the safety of the system. Optionally, the third helical section 306a may also be implemented as an electrical resistance wire or an induction coil, which can deliver heat energy when energized. The third longitudinally extending section 306b may also be a wire arranged along the wall of the fluid transportation pipe 305 and has its proximal end coupled to an electrical input/output interface on the proximal end of the catheter body. In this way, it is connected to the control device 100 or the ablation energy output device 200 and thus able to receive inputted external power.

With continued reference to FIG. 3c, the electrophysiology catheter 300 further includes a second temperature sensor 307. The second temperature sensor 307 may be disposed at the proximal end of the catheter body 301 to capture temperature information of the catheter body 301. Alternatively, the second temperature sensor 307 may be arranged on the second heating component 306 so as to capture temperature information of the second heating component 306. Still alternatively, two or more second temperature sensors 307 may be provided at the proximal end of the catheter body 301 and on the second heating component 306 in order to capture temperature information of both catheter body 301 and the second heating component 306. In addition, the temperature information fed back by the second temperature sensor 307 may be fed back to the control device 100 through the electrical connection link. The control device 100 in turn controls temperature of the second heating component 306 based on the temperature information fed back by the second temperature sensor 307. Preferably, the second temperature sensor 307 is provided on the fluid transportation pipe 305 and is arranged at a location close to a distal end of the second heating component 306, more specifically, to a distal end of the third helical section 306a of the second heating component 306. In case of a plurality of second heating component 306 being provided, a second temperature sensor 307 may be arranged between the third helical sections 306a of the second heating component 306. Likewise, the number and positions of the second temperature sensors 307 may vary depending on the actual requirements, which is not limited in present application.

Referring to FIGS. 3a and 3c, the electrophysiology catheter 300 further includes a handle 308, which is arranged on the catheter body 301 at the proximal end thereof and configured to control rotation, bending or other actions of the catheter body 301. Besides, a plurality of interfaces are provided on the handle 308, preferably including at least one electrical input/output interface, at least one fluid inlet interface, at least one fluid outlet interface and at least one lumen interface. In embodiments of the present application, the handle 308 includes: one lumen interface 3081 configured to introduce a guidewire, a mapping catheter, a contrast medium or another instrument or material; two electrical input/output interfaces, including a heating energy input/output interface 3082 and temperature sensor communication interface 3083; one fluid inlet interface 3084 and one fluid outlet interface 3085.

All heating components may be connected to the same heating energy input/output interface 3082. In this case, the heating energy input/output interface 3082 is provided with different current channels for which respective heating components use. All temperature sensors may be connected to the same temperature sensor communication interface 3083. In this case, the temperature sensor communication interface 3083 is also provided with different data channels for which respective temperature sensors use. The fluid inlet interface 3084 is in fluid communication with the fluid transportation pipe 305 and connected to the ablation energy output device 200 so that a fluid supplied by the ablation energy output device 200 is able to be introduced into the electrophysiology catheter 300. The fluid outlet interface 3085 is in fluid communication with the aforementioned fluid exhaust pipe of the catheter body 301 so as to drain the fluid after ablation out of the catheter.

Furthermore, the catheter body 301 further includes an outer tube 309 and a core shaft 310. The handle 308 is arranged on the outer tube 309. The fluid transportation pipe 305 and the core shaft 310 are arranged side by side and sleeved in the outer tube 309. The core shaft 310 is hollow and movably disposed in the outer tube 309. The handle 308 may be manipulated to cause the core shaft 310 to move in the outer tube 309, so as to achieve release of the balloon 302 from a sheath and retraction and withdrawal of the balloon 302 into the sheath. The proximal end of the core shaft 310 is in communication with the lumen interface 3081 of the handle 308 for delivering related instruments, such as guidewires, mapping catheters or contrast fluids. In practical use, a distal end of the core shaft 310 protrudes out of a distal end of the outer tube 309 and is connected to a distal end of the balloon 302, while the proximal end of the balloon 302 is connected to the outer tube 309 and the fluid exhaust pipe is arranged between the core shaft 310 and outer tube 309. Preferably, a radiopaque marker 311 made of a metallic, radiopaque material is disposed at the distal end of the core shaft 310. During operation, the physician can confirm the position of the balloon 302 relative to the sheath via the radiopaque marker 311 using a fluoroscopic imaging device. In an embodiment of the present application, the fluid transportation pipe 305 is bonded to the exterior of the core shaft 310. However, alternatively, the fluid transportation pipe 305 may be secured to the core shaft 310 only by means of the first helical section 305a that is wound around the core shaft 310. In this case, the fluid transportation pipe 305 and the core shaft 310 are axially movable relative to each other.

Figure 3D:
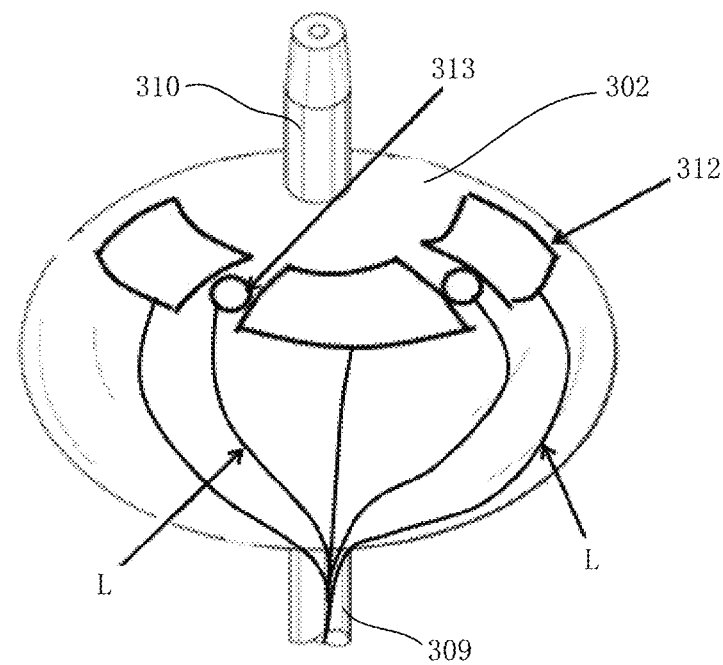
FIG. 3d is a structural schematic of a balloon according to an embodiment of the present application.

Referring to FIG. 3d, in conjunction with FIG. 3a, the electrophysiology catheter 300 further includes a third heating component 312, which is disposed on the balloon 302 to heat a target zone Q. The target zone Q is a heating zone on the target tissue. The third heating component 312 may be arranged on the outer surface or inner surface of the balloon 302 or between the outer and inner surfaces of a double-layer balloon. The third heating component 312 is preferably disposed on the inner surface, or between the inner and outer surfaces, of the balloon 302, so as to avoid removal of the third heating component 312 due to direct contact with the target tissue and improve the safety of the product. The plurality of third heating component 312 may be provided and preferably distributed on the balloon 302 uniformly, for example, in a circumference direction of the balloon 302. Depending on the actual requirements, all or some of the third heating component 312 may be activated at the same time to perform heating. It is to be noted that the number and positions of the third heating components 312 may be determined according to the actual requirements. Optionally, the third heating component 312 may be an ablation electrode that is connected by a lead L to the heating energy input/output interface 3082 at the proximal end of the electrophysiology catheter 300.

Further, the electrophysiology catheter 300 also includes one or more third temperature sensors 313, which are also disposed on the balloon 302 to capture temperature information of the third heating component 312. Preferably, the third temperature sensors 313 are arranged in the vicinity of the third heating component 312. For example, each third temperature sensor 313 may be disposed between adjacent third heating components 312. The temperature information fed back by the third temperature sensors 313 may be fed back to the control device 100. The control device 100 in turn controls heating temperature of the third heating component 312 based on the temperature information of the third heating component 312 fed back by the third temperature sensors 313, so as to control ablation temperature of the tissue. Here, the temperature information of the third heating component 312 indicates temperature information of the balloon surface.

Furthermore, the electrophysiology catheter 300 also includes a fourth temperature sensor 314 for capturing temperature information of the balloon 302 or of the catheter body 301. The fourth temperature sensor 314 is disposed on the balloon 302 or on the catheter body 301. Alternatively, two or more fourth temperature sensors 314 are provided respectively on the balloon 302 and on the catheter body 301. In case that the fourth temperature sensor 314 is provided on the catheter body 301, it may be specifically arranged at the distal end of the core shaft 310 and is located in the balloon 302. The fourth temperature sensor 314 is coupled to the temperature sensor communication interface 3083 on the handle 308, which may be in turn coupled to the control device 100. In this way, the control device 100 is able to control a cryoablation or thermal ablation temperature based on the temperature information of the balloon fed back by the fourth temperature sensor 314. It is to be noted that the temperature sensors discussed above may be either all connected to a single temperature sensor communication interface or to different temperature sensor communication interfaces. Likewise, the above-described heating component may be either all connected to a single heating energy input/output interface or to different heating energy input/output interfaces.

Further, the ablation system 10 also includes a display device, which is connected to the control device 100 and configured to display the temperature information fed back by any one of the first, second, third and fourth temperature sensors 304, 307, 313 and 314 in real time, so that the physician is able to adjust cryoablation or thermal ablation energy based on these temperature information.

A more detailed description of the structure and working process of the ablation system 10 will be set forth below with reference to FIGS. 5 to 7.

Figure 5:
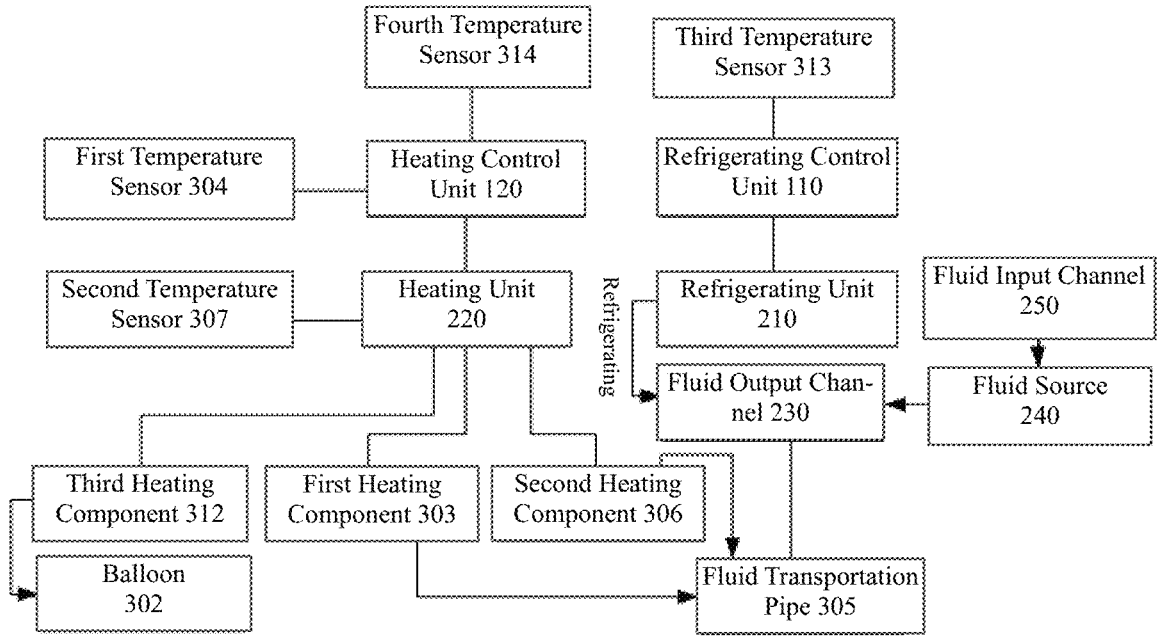
FIG. 5 shows a block diagram of the ablation system according to a preferred embodiment of the present application.

FIG. 5 shows a block diagram of a preferred ablation system 10 according to this embodiment. As shown in FIG. 5, the control device 100 includes a control unit, which preferably includes a refrigerating control unit 110 and a heating control unit 120. The ablation energy output device 200 preferably includes a refrigerating unit 210, a heating unit 220, a fluid output channel 230, a fluid source 240 and a fluid input channel 250.

In particular, the fluid source 240 may be a reservoir for storing an ablation fluid, preferably carbon dioxide or nitrous oxide. The usage of the carbon dioxide or nitrous oxide enables to effectively shorten the time required for natural temperature recovery following each ablation cycle, resulting in an improvement in operation efficiency. The fluid source 240 communicates with each of the fluid input channel 250 and the fluid output channel 230. The fluid input channel 250 is configured to introduce a fluid from an external source into the fluid source 240. However, in practical applications, it is possible to omit the fluid input channel 250. The fluid output channel 230 is be configured to transport the fluid from the fluid source 240 into the electrophysiology catheter. In particular, the fluid output channel 230 is connected to the fluid inlet interface 3084 of the electrophysiology catheter 300.

The refrigerating unit 210 is disposed on the fluid output channel 230 in order to refrigerate the fluid in the fluid output channel 230. The refrigerating unit 210 may be a compressor or another type of refrigerating device, and the present application is not limited to any particular type of refrigerating device. The refrigerating unit 210 is configured to be communicatively coupled to the refrigerating control unit 110, so that the refrigerating control unit 110 is able to control the working state of the refrigerating unit 210.

The heating unit 220 is configured to be electrically connected to the electrophysiology catheter 300 to provide heat energy to all or some of the aforementioned heating components. In particular, the heating unit 220 is connected to the heating energy input/output interface 3082 on the electrophysiology catheter 300. In addition, the heating unit 220 is also configured to be communicatively connected to the heating control unit 120, so that the heating control unit 120 is able to control the working state of the heating unit 220. The heating unit 220 may be a high-frequency energy source (high-frequency heating power supply) that is electrically connected to at least one of the first, second and third heating components 303, 306, 312 on the electrophysiology catheter 300, so as to provide these heating components with a high-frequency, high-voltage current for heating. The heating unit 220 may also be a normal power source that is electrically connected to at least one of the first and second heating components 303, 306 on the electrophysiology catheter 300, so as to provide the heating components with a heating current. The heating current may be either an AC or DC current.

In practical use, the refrigerating and heating units 210, 220 may operate simultaneously. For example, in the operation of a thermal ablation, each of refrigerating and heating units 210, 220 operates normally. At this time, the refrigerating unit 210 supplies the frozen liquid to the electrophysiology catheter 300 via the fluid output channel 230, and concurrently, the heating unit 220 provides a current to the first heating component 303 or to each of the first and second heating component 303, 306 on the electrophysiology catheter 300, so that the frozen liquid flowing through the electrophysiology catheter 300 is transformed into a thermal ablation gas after heated by the heating components and is sprayed onto the balloon 302. Preferably, in some embodiments, during the thermal ablation, the refrigerating unit 210 does not operate while the heating unit 220 operates normally. At this time, the fluid output channel 230 supplies a first fluid (a gas, liquid or gas/liquid mixture) to the electrophysiology catheter 300, and concurrently, the heating unit 220 provides a current to the first heating component 303 or to each of the first and second heating component 303, 306 on the electrophysiology catheter 300, so that the first liquid flowing through the electrophysiology catheter 300 is transformed into a thermal ablation gas after heated by the heating components and is sprayed onto the balloon 302. However, it will be appreciated that, in a cryoablation, only the refrigerating unit 210 operates to refrigerate while the heating unit 220 does not work.

More particularly, the refrigerating control unit 110 is configured to control, upon the receipt of a cryoablation instruction, the refrigerating unit 210 to operate to supply a frozen liquid (i.e., the second fluid) to the electrophysiology catheter 300 via the fluid output channel 230. The heating control unit 120 is configured to control, upon the receipt of a thermal ablation instruction, the heating unit 220 to operate, concurrently with the refrigerating unit 210 selectively operating or not operating under the control of the refrigerating control unit 110. As a result, the fluid output channel 230 provides the electrophysiology catheter 300 with the first fluid which is in turn heated in the fluid transportation pipe 305 and then sprayed to the inner surface of the balloon 302. In embodiments of the present application, thermal ablation button and cryoablation button may be provided on the handle 308, or a computer interface. In this case, the physician starts the thermal ablation button to launch a thermal ablation instruction to the heating control unit 120, or the physician starts the cryoablation button to launch a cryoablation instruction to the refrigerating control unit 110. The computer interface may be provided on the control device 100 or on the ablation energy output device 200.

In a non-limiting operation, refrigerating control unit 110 sends a refrigerating signal to the refrigerating unit 210 that starts to refrigerate upon receipt of the refrigerating signal. Likewise, heating control unit 120 sends a heating signal to the heating unit 220 that starts to heat at least one of the first, second and third heating component 303, 306, 312 by outputting current upon receipt of the heating signal.

Further, during the cryoablation, the refrigerating control unit 110 controls, according to temperature information fed back by either or both of the fourth and third temperature sensors 314, 313, the refrigerating unit 210 to regulate the refrigerating temperature, so that the surface temperature of the balloon is controlled within the predetermined cryoablation temperature range.

Further, during the thermal ablation, the heating control unit 120 controls, according to temperature information fed back by at least one of the first, second, third and fourth temperature sensors 304, 307, 313, 314, the heating unit 220 to regulate heating temperature of at least one of the first and second heating component 303, 306, so that the surface temperature of the balloon is controlled within the predetermined thermal ablation temperature range.

Furthermore, during the thermal ablation, the heating control unit 120 controls, according to temperature information fed back by either or both of the third and fourth temperature sensors 313, 314, the heating unit 220 to regulate the heating temperature of the third heating component 312, so as to control a temperature of the third heating component 312 in the thermal ablation of a target tissue.

In embodiments of present application, the ablation system 10 includes a cryoablation mode and a thermal ablation mode.

Figure 6:
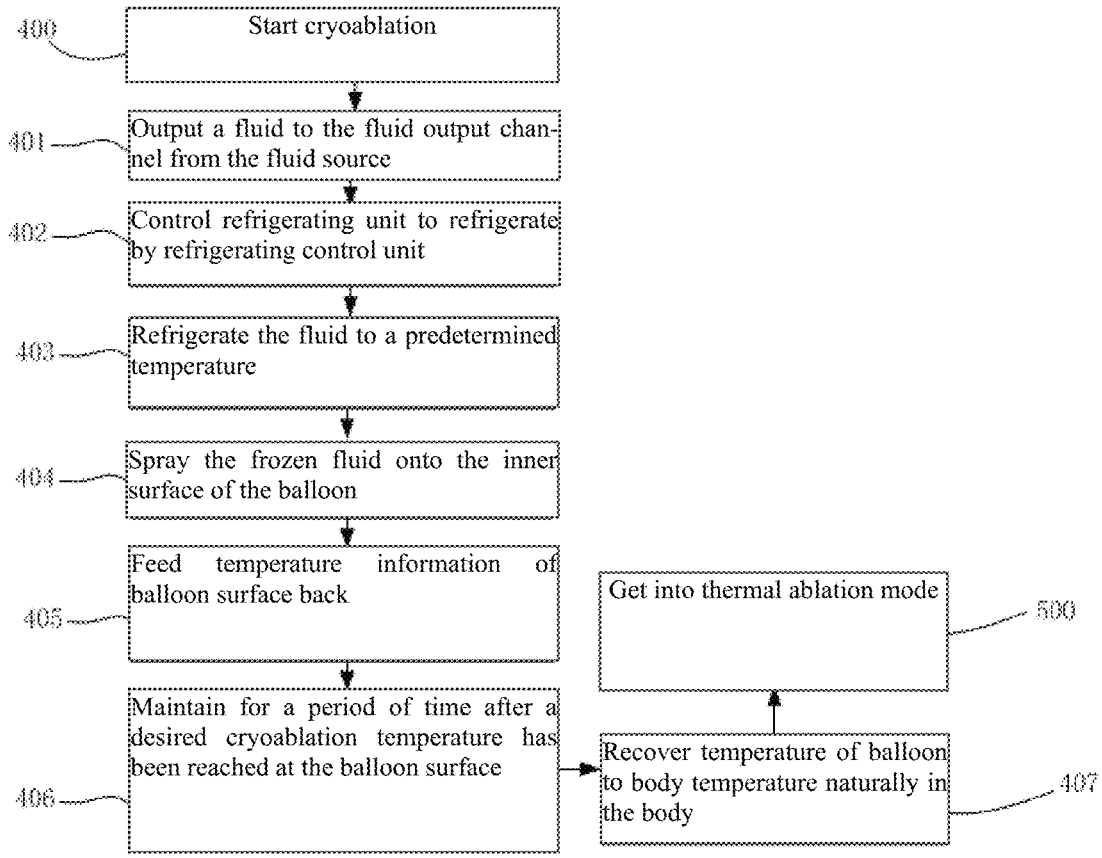
FIG. 6 is a flowchart of the ablation system according to an embodiment of the present application operating in a cryoablation mode.

In one embodiment, as shown in FIG. 6, as the ablation system 10 gets into the cryoablation mode, it starts the cryoablation process of step 400. The cryoablation process including following steps:

Step 401: Outputting a fluid to the fluid output channel from the fluid source.

Step 402: Controlling, by the refrigerating control unit, the refrigerating unit to refrigerate.

Step 403: Refrigerating the fluid to a predetermined refrigeration temperature.

Step 404: Spraying the frozen fluid onto the inner surface of the balloon. Here, Steps 401, 402, 403 and 404 may be performed simultaneously. That is, the frozen liquid is sprayed onto the inner surface of the balloon at the beginning of refrigerating.

Step 405: Controlling, by refrigerating control unit, the refrigerating temperature of the refrigerating unit in real time during the refrigeration process based on the temperature information fed back by at least one of the third and fourth temperature sensors 313, 314.

Step 406: Ending the process after a desired cryoablation temperature (e.g., from −10° C. to −60° C.) has been reached at the balloon surface and maintained for a period of time (e.g., 120-180 seconds).

Following the completion of this cryoablation process, the physician may determine to perform another cryoablation process or to directly get into the thermal ablation mode (step 500) according to actual effect of the cryoablation. However, it will be appreciated that after each cryoablation, the balloon 302 needs to recover to body temperature naturally in the body in advance (step 407) before the next cryoablation can be performed.

Figure 7:
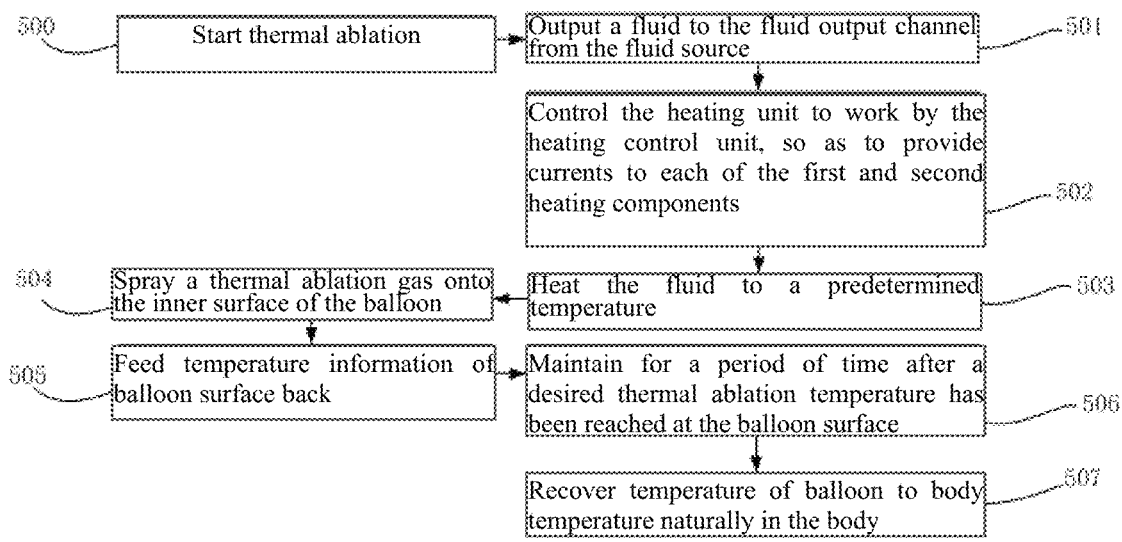
FIG. 7 is a flowchart of the ablation system according to an embodiment of the present application operating in a thermal ablation mode.

In another embodiment, as shown in FIG. 7, as the ablation system 10 gets into the thermal ablation mode, it starts the thermal ablation process of step 500. The thermal ablation process including following steps:

Step 501: Outputting a fluid to the fluid output channel from the fluid source.

Step 502: Controlling, by the heating control unit, the heating unit to work so as to provide a current to the first heating component or to provide currents to each of the first and second heating components.

Step 503: Heating the fluid to a predetermined heating temperature through two times of heating.

Step 504: Spraying a thermal ablation gas onto the inner surface of the balloon. Here, Steps 501, 502, 503 and 504 may be performed simultaneously. That is, the thermal ablation gas is sprayed onto the inner surface of the balloon at the beginning of heating.

Step 505: Controlling, by the heating control unit 120, the current output from the heating unit 220 in real time during the heating process based on temperature information fed back by at least one of the first, second, third and fourth temperature sensors 304, 307, 313, 314, so as to adjust the heating temperature of the first heating component 303 or the heating temperatures of both the first heating component 303 and second heating component 304.

Step 506: Ending the process after a desired thermal ablation temperature (e.g., 50° C.-80° C.) has been reached at the balloon surface and maintained for a period of time (e.g., 10-50 seconds). Similarly, after each thermal ablation, the balloon needs to recover to body temperature naturally in the body (step 507).

In another embodiment, as the ablation system 10 gets into the thermal ablation mode, the thermal ablation may also be implemented in the following approach: controlling, by the heating control unit 120, the heating unit 220 to work to output a high-frequency, high-voltage current to the third heating component 312, so that the third heating component 312 utilizes the ablation electrode to cauterize the target tissue and thus achieves the purpose of ablating tissues with abnormal electrocardiographic activities. In one embodiment of the present application, when the third heating component 312 works, the ablation energy output device 200 still supplies the first fluid to the electrophysiology catheter 300, meanwhile the first and second heating components 306 continue to work. In this way, the electrophysiological catheter 300 is able to cauterize the target tissue through the third heating element 312 while spraying the thermal ablation gas, so as to realize the thermal ablation of the target tissue. In some other embodiments, when the third heating component 312 works, the ablation energy output device 200 stops to provide the electrophysiology catheter 300 with any fluid, allowing the third heating component 312 to perform the thermal ablation on the target tissue alone.

At last, the preferred embodiments of the present invention are as described above, but the scope of the present application is not limited to the above embodiments. For example, the ablation energy output device 200 and the control device 100 may be integrated in a single apparatus in which the two devices may be communicatively connected to each other. As another example, the control unit may be implemented as a conventional controller, processor or similar control device. In addition, the temperature sensor may be implemented as a thermocouple, and the balloon may be implemented as either a single-layer or double-layer balloon. The balloon may be equipped with a mapping electrode. Besides, in preferred embodiments, the physician may adjust temperatures of respective heating components mainly based on the balloon temperature information fed back by the fourth temperature sensor combining with the temperature information of respective heating components fed back by respective temperature sensors. In this way, the device is able to be adjusted quickly and accurately, resulting in a high temperature adjustment efficiency and good performance. Further, all the temperatures fed back by the temperature sensors may be displayed on a screen in real time to facilitate the physician to observe. This makes temperature adjustments even more intuitive and convenient.

The technical features of the above-mentioned embodiments may be combined arbitrarily. While not all possible combinations of these features of the above-mentioned embodiments are described for the sake of brevity, they are all considered within the protection scope of this specification as long as there is no contradiction therein.

The foregoing embodiments represent merely a few embodiments of present application, and while they have been described above specifically and in detail, they are not intended to be understood as limiting the protection scope of present application. It is noted that, some variations and modifications can be made by those of ordinary skill in the art without departing from the spirit of the present application, which all fall into the protection scope of present application. Therefore, the protection scope of present application is defined by the appended claims.

What is claimed is:

1. A balloon catheter, comprising a catheter body and a balloon that is disposed at a distal end of the catheter body, wherein the balloon catheter further comprises a first heating component and a first temperature sensor and the catheter body comprises a fluid transportation pipe, wherein the fluid transportation pipe has a distal end disposed within the balloon to release a fluid into the balloon, the first heating component arranged at the distal end of the fluid transportation pipe to heat the fluid in the fluid transportation pipe, the first temperature sensor arranged at the distal end of the catheter body or on the first heating component to capture temperature information of the catheter body or the first heating component, and wherein:

when the first heating component is operating, the fluid transportation pipe is configured to release a thermal ablation gas into the balloon; and when the first heating component is not operating, the fluid transportation pipe is configured to release a freezing liquid into the balloon, wherein the fluid transportation pipe comprises a first helical section and a first longitudinally extending section in communication with the first helical section, wherein the first heating component is disposed on the first longitudinally extending section, and wherein the first temperature sensor is arranged on the fluid transportation pipe at a location close to a distal end of the first heating component, and wherein the first helical section is provided with a plurality of fluid spraying orifices, and wherein the plurality of fluid spraying orifices are configured to spray the fluid towards different directions.

2. The balloon catheter of claim 1, further comprising a second heating component and a second temperature sensor, wherein the second heating component is disposed at a proximal end of the fluid transportation pipe to pre-heat the fluid entering the fluid transportation pipe, the second temperature sensor disposed at a proximal end of the catheter body or on the second heating component to capture temperature information of the catheter body or the second heating component, wherein:

when the first and second heating components are operating concurrently, the fluid transportation pipe is configured to release a thermal ablation gas into the balloon; when none of the first and second heating component is operating, the fluid transportation pipe is configured to release a freezing liquid into the balloon.

3. The balloon catheter of claim 2, further comprising a handle coupled to the proximal end of the catheter body, wherein the second heating component is disposed within the handle.

4. The balloon catheter of claim 3, wherein the handle comprises at least one electrical input/output interface, one fluid inlet interface and one fluid outlet interface, wherein the fluid inlet interface is in communication with the proximal end of the fluid transportation pipe, the at least one electrical input/output interface coupled to the first heating component, the first temperature sensor, the second heating component and the second temperature sensor, the fluid outlet interface configured to exhaust the fluid in the catheter body out of the catheter body.

5. The balloon catheter of claim 2, wherein the second temperature sensor is disposed on the fluid transportation pipe at a location close to a distal end of the second heating component.

6. The balloon catheter of claim 2, wherein the first and/or second heating component are/is an electrical resistance wire or induction coil.

7. The balloon catheter of claim 2, further comprising a third heating component and a third temperature sensor, the third heating component disposed on the balloon to heat a target zone, the third temperature sensor disposed on the balloon to capture temperature information of the third heating component.

8. The balloon catheter of claim 7, further comprising at least one fourth temperature sensor disposed on the balloon and/or on the catheter body to capture temperature information of the balloon and/or catheter body.

9. The balloon catheter of claim 1, wherein the first heating component comprises a second helical section and a second longitudinally extending section electrically connected to the second helical section, wherein the second helical section is wound around the fluid transportation pipe, and the second longitudinally extending section extends along a pipe wall of the fluid transportation pipe and comes into connection with an electrical input/output interface at the proximal end of the catheter body.

10. The balloon catheter of claim 1, wherein the catheter body further comprises an outer tube and a hollow core shaft, each of the fluid transportation pipe and the core shaft sleeved within the outer tube, the core shaft movably arranged within the outer tube, wherein the balloon has its distal end to be connected to the core shaft and proximal end to be connected to the outer tube, and wherein a distal end of the fluid transportation pipe is helically wound around the core shaft.

11. An ablation system comprising a control device, an ablation energy output device and the balloon catheter according to claim 1, the ablation energy output device being in communication with the balloon catheter to supply a fluid to the balloon catheter, wherein, the control device is configured to control the ablation energy output device to selectively supply a first or second fluid to the fluid transportation pipe, the second fluid being the freezing liquid, the control device is further configured to, when the ablation energy output device supplies the first fluid to the fluid transportation pipe, control the first heating component to operate such that the first heating component heats the first fluid entering the fluid transportation pipe to make the fluid transportation pipe spray the thermal ablation gas to the balloon; and simultaneously control a heating temperature of the first heating component based on temperature information fed back by the first temperature sensor such that a surface temperature of the balloon is in a predetermined thermal ablation temperature range, the control device is further configured to, when the ablation energy output device supplies the second fluid to the fluid transportation pipe, control the first heating component not to operate such that the fluid transportation pipe sprays the freezing liquid to the balloon.

12. The ablation system of claim 11, wherein the balloon catheter further comprises a second heating component and a second temperature sensor, the second heating component disposed at a proximal end of the fluid transportation pipe, the second temperature sensor disposed at a proximal end of the catheter body or on the second heating component, and wherein, the control device is also configured to, when the ablation energy output device supplies the first fluid to the fluid transportation pipe, further control the second heating component to operate such that the second heating component pre-heats the fluid just entering the fluid transportation pipe; and simultaneously control a heat temperature of the second heating component based on temperature information fed back by the second temperature sensor.

13. The ablation system of claim 12, wherein the ablation energy output device comprises a fluid source, a heating unit, a refrigerating unit and a fluid output channel, wherein the fluid source is configured to store fluid, and the fluid output channel is in communication with the fluid source to transport the fluid in the fluid source, wherein the refrigerating unit is disposed on the fluid output channel to refrigerate the fluid in the fluid output channel, and the heating unit is configured to provide the first heating component and/or second heating component with a heating energy, wherein the control device is further configured to, when the ablation energy output device supplies the second fluid to the fluid transportation pipe, control the refrigerating unit to refrigerate the fluid flowing in the fluid output channel such that the ablation energy output device supplies the fluid transportation pipe with the freezing liquid, wherein the control device is further configured to, when the ablation energy output device supplies the first fluid to the fluid transportation pipe, control the heating unit to provide the first heating component with a heating energy such that the first heating component heats the fluid flowing in the fluid output channel or to provide the first and second heating components with a heating energy such that the first and second heating components heat the fluid flowing in the fluid output channel.

14. The ablation system of claim 13, wherein the predetermined thermal ablation temperature range is from 50° C. to 80° C.

15. The ablation system of claim 13, wherein the control device comprises a refrigerating control unit and a heating control unit, and wherein the refrigerating unit is configured to refrigerate the fluid flowing in the fluid output channel based on a refrigerating signal sent from the refrigerating control unit; and wherein the heating unit is configured to supply the first heating component and/or the second heating component with heating energy based on a heating signal sent from the heating control unit.

16. The ablation system of claim 13, wherein the balloon catheter further comprises a third heating component and a third temperature sensor, which are both disposed on the balloon, and wherein the control device is further configured to, when the ablation energy output device stops supplying the fluid to the fluid transportation pipe or starts to supply the first fluid to the fluid transportation pipe, control the heating unit to provide the heating energy to the third heating component such that the third heating component heats a target tissue, and simultaneously control a heating temperature of the third heating component based on temperature information of the third heating component fed back by the third temperature sensor.

17. The ablation system of claim 16, wherein the balloon catheter further comprises at least one fourth temperature sensor disposed on the balloon and/or on the catheter body, and wherein the control device is further configured to modulate a cryoablation temperature or a thermal ablation temperature based on temperature information of the balloon and/or catheter body fed back by the at least one fourth temperature sensor.

18. The ablation system of claim 12, wherein the control device is configured to, control the ablation energy output device to supply the second fluid to the balloon catheter for a duration of time and then to supply the first fluid to the balloon catheter, and simultaneously control the ablation energy output device to supply the first heating component with a heating energy or to supply the first heating component and the second heating component with a heating energy, so as to perform at least one thermal ablation cycle following at least one cryoablation.

* * * * *